(12) United States Patent
Okado

(10) Patent No.: US 8,075,768 B1
(45) Date of Patent: Dec. 13, 2011

(54) LIQUID CHROMATOGRAPH DEVICE

(75) Inventor: Takao Okado, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 13/107,683

(22) Filed: May 13, 2011

(30) Foreign Application Priority Data

Jul. 1, 2010 (JP) .................... 2010-150841

(51) Int. Cl.
*B01D 15/08* (2006.01)

(52) U.S. Cl. ....... 210/198.2; 210/85; 210/143; 210/181; 95/87; 96/102

(58) Field of Classification Search .............. 210/635, 210/656, 659, 85, 101, 143, 181, 198.2; 95/87; 96/101, 102
See application file for complete search history.

(56) References Cited

U.S. PATENT DOCUMENTS

| | | | |
|---|---|---|---|
| 4,088,458 A * | 5/1978 | Jourdan | 96/102 |
| 4,966,695 A * | 10/1990 | Joshua | 210/198.2 |
| 6,355,165 B1 * | 3/2002 | Sutton et al. | 210/198.2 |
| 6,485,543 B1 * | 11/2002 | MacDonald et al. | 95/87 |
| 6,530,260 B1 * | 3/2003 | Mustacich et al. | 73/23.41 |
| 2002/0153312 A1 * | 10/2002 | Gjerde et al. | 210/635 |
| 2005/0258088 A1 * | 11/2005 | Botelho et al. | 210/198.2 |
| 2008/0314812 A1 * | 12/2008 | Kareh et al. | 210/198.2 |

FOREIGN PATENT DOCUMENTS

JP 2000-111536 4/2000

* cited by examiner

*Primary Examiner* — Ernest G Therkorn
(74) *Attorney, Agent, or Firm* — DLA Piper LLP (US)

(57) ABSTRACT

A liquid chromatograph device was provided wherein operations inside a thermostatic chamber can be safely performed even while a heat block is being heated. The liquid chromatograph device comprises: a thermostatic chamber; outer doors and that are disposed at the front surface of the thermostatic chamber; a heat block; heater for heating said heat block; temperature sensor for the heat block; flowing means for flowing air between the inside and outside of the thermostatic chamber; a control means for controlling the supply of power to the heater based on the result of the temperature sensor; and an inner door between the outer door and the heat block, the inner door comprising a hollow inner door main body, a heat-insulating material that is housed within the inner door so as to form an air chamber between the heat-insulating material and the surface of the outer door of the inner door main body and inlet/outlet slits and that are formed in the inner door main body. These slits and the flowing means causes air within the inner door to flow out, thus reducing the temperature of the inner door.

5 Claims, 4 Drawing Sheets

LIQUID CHROMATOGRAPH DEVICE

The present invention relates to a liquid chromatograph device and in particular to a thermostatic chamber that maintains the temperature of a separation column to a predetermined temperature.

BACKGROUND TECHNOLOGY

An important aspect of analyses that use liquid chromatograph device is controlling the temperature of the separation column. Various methods are used as a heating system for the separation column including the heat block method, air circulation method and the liquid circulation method.

With the heat block method, a heat block made of a highly thermally conductive material such as aluminum is brought into close contact with a separation column inside a thermostatic chamber. The temperature of the heat block itself is adjusted using a heater and the like. The temperature of the heat block is detected with a temperature sensor, and the detected result is used to adjust the electrical power that is supplied to the heater (see Patent Literature 1).

In a typical thermostatic chamber of a liquid chromatograph apparatus, the heat block is situated right there when the outer door of the thermostatic chamber is opened. The construction is such that even when the heat block is at a high temperature, the heat block can be directly touched by the user's hands when the outer door of the thermostatic chamber is open.

PRIOR ART LITERATURE

Patent Literature

Patent Literature 1: JP 2000-111536 A

OVERVIEW OF THE INVENTION

Problems to Be Solved by the Invention

One possible way of preventing the user's hands from directly touching a heated heat block is to provide an inner door between the heat block and the outer door of the thermostatic chamber. However, since the inner door itself is also heated by the heat block, the risk remains of the user's hands touching the outer surface of the inner door.

The present invention was made in light of these problems, and it is the object of the present invention to provide a device that allows a user to open the outer door of a thermostatic chamber and safely perform manipulations therein even while the heat block in a thermostatic chamber of a liquid chromatograph device is being heated.

Means for Solving the Problems

According to a first mode of the present invention that was made to solve the afore-described problems, the liquid chromatograph device includes:
 a thermostatic chamber;
 one or a plurality of outer doors that are disposed at the front surface of the thermostatic chamber;
 a heat block that is disposed in the thermostatic chamber for heating a separation column;
 a heating means for heating the heat block;
 a temperature detection means for detecting the temperature of the heat block;
 a flowing means for flowing air between the inside and outside of the thermostatic chamber;
 a control means for controlling the supply of power to the heating means based on the detection result of the temperature detection means; and
 an inner door between the outer door and the heat block, the inner door comprising a hollow inner door main body, a heat-insulating material that is housed within the inner door main body so as to form an air chamber at least between the heat-insulating material and the surface on the outer door side of the inner door main body, and outlet slits and inlet slits that are formed in the inner door main body;
 wherein the flowing means causes air to flow from the outer door side through the inlet slit into the air chamber and air inside the air chamber to flow through the outlet slit to the heat block side.

A second mode of a liquid chromatograph device according to the present invention made to solve the afore-described problems is the liquid chromatograph device according to the first mode further including a plurality of outer door open detection means to detect, if, at least, one of said outer doors is open wherein the control means stops the supply of power to the heating means if the outer door open detection means detects that the outer door is open.

A third mode of a liquid chromatograph device according to the present invention made to solve the afore-described problems is the liquid chromatograph device according to the second mode further including an alarm sound generation means for generating an alarm sound wherein the control means causes the alarm sound generation means to generate an alarm sound if the outer door open detection means detects that the outer door is open when the temperature detected by the temperature detection means is higher than a predetermined temperature.

A fourth mode of a liquid chromatograph device according to the present invention made to solve the afore-described problems is the liquid chromatograph device according to the second mode further including an alarm display lamp disposed on the front surface of the thermostatic chamber wherein the control means causes the alarm display lamp to flash if the outer door open detection means detects that the outer door is open when the detected result by the temperature detection means is higher than a predetermined temperature.

A fifth mode of a liquid chromatograph device according to the present invention made to solve the afore-described problems is the liquid chromatograph device according to the second mode further including a cooling means for cooling the heat block wherein the control means instructs the cooling means to cool the heat block when the outer door open detection means detects that the outer door is open.

Effects of the Invention

The heat emanating from the heat block is shielded to some extent by the heat-insulating means that is disposed within the inner door but completely shielding it is difficult. With a liquid chromatograph device according to the first mode of the present invention, an air chamber is formed on the outer door side of the heat-insulating material in the inner door. Air flows into the air chamber through the inlet slit from the outer door side, and the air in the air chamber flows out through the outlet slit to the heat block side. This greatly reduces the temperature of the outer surface of the inner door.

With the second mode which includes a plurality of means for detecting when the outer door of the liquid chromatograph device is open, if the outer door is detected to be open, power supply to the heating means is stopped, thus stopping the heating of the heat block. Furthermore, by providing a plurality of outer door open detection means for detecting if, at least, one of said outer doors is open, even if one of the outer door open detection means should fail, the heating of the heat block is stopped with certainty.

Furthermore, with the third and fourth modes including an alarm display lamp and a means for generating an alarm sound, when the temperature of the heat block exceeds a predetermined temperature and the outer door open detection means detects that the outer door is open, an alarm sound is generated or an alarm display lamp flashes, thus warning the user by sight and sound that the heat block is at a high temperature and urging a safe handling.

Furthermore, with the fifth mode which includes a means for cooling the heat block, when outer door open detection means detects that the outer door is opened, cooling of the heat block is initiated. Hence, even if the user were to inadvertently touch the heat block, the risk of a burn injury is reduced.

EMBODIMENTS OF THE INVENTION

Figure 1:
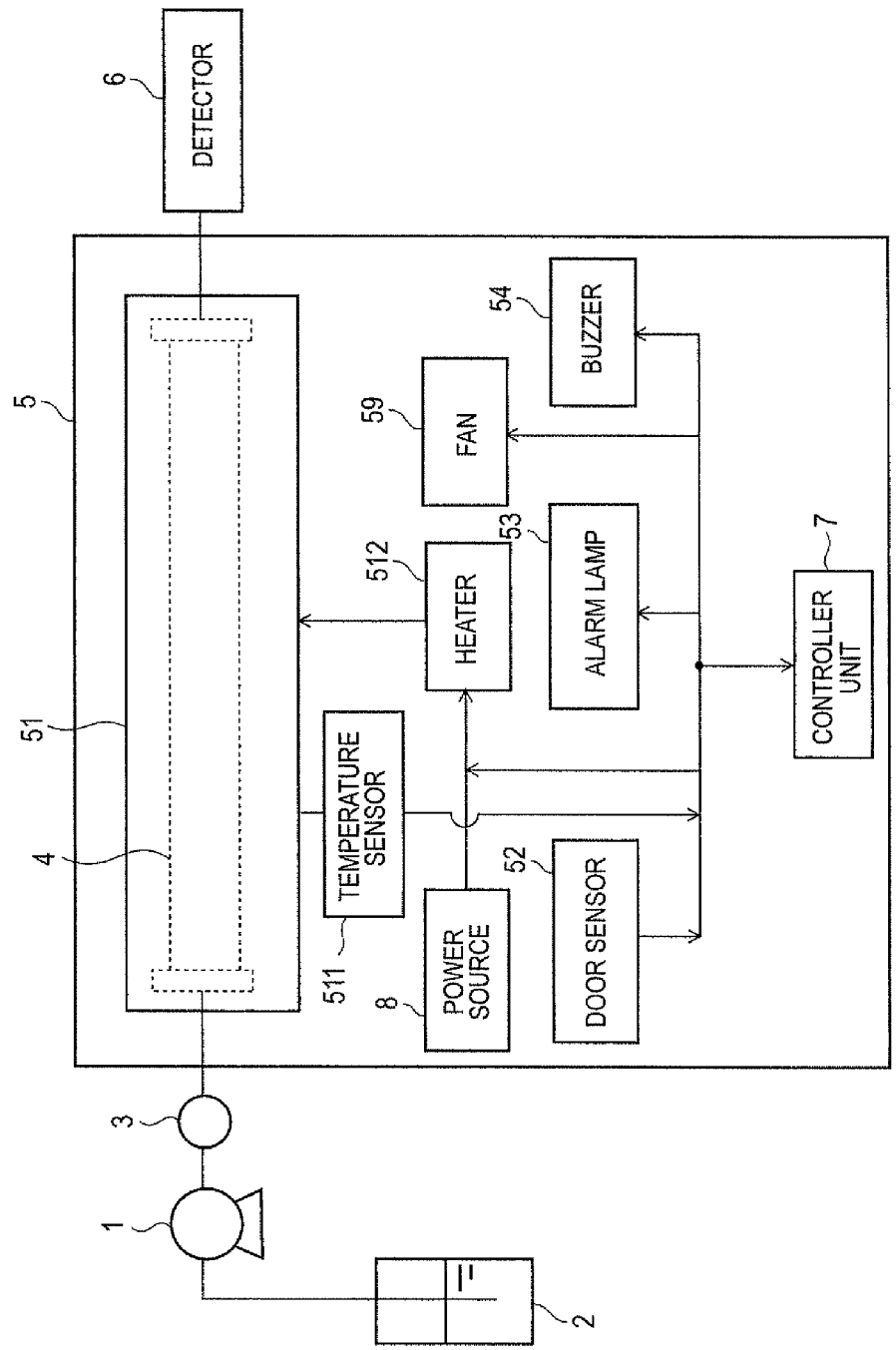
FIG. 1 shows the configuration of the main components of a liquid chromatograph device according to the present invention.

Embodiments of the present invention are described next with reference to FIG. 1 through FIG. 4, Embodiments FIG. 1 shows the configuration of the main components of a liquid chromatograph device according to the present invention. The fluid transport pump 1 draws in the mobile phase that is stored in a mobile phase vessel 2 and supplies the mobile phase to column 4 at a predetermined flow rate via an auto-sampler 3. The auto-sampler 3 which includes an injector selects the specified sample out of a plurality of samples that are readied in advance and injects the sample into the mobile phase. The injected sample is transported by the mobile phase and is introduced into column 4. The sample then elutes out from the column 4, separated in the time direction by the time required in passing through the column 4. The column 4 is housed in a thermostatic chamber 5 whose temperature can be adjusted to a constant temperature. The eluate emerging from the column 4 is introduced to a detector 6 such as an absorption spectrophotometer which detects signals over time corresponding to individual components in the eluate.

Disposed in the thermostatic chamber 5 are: a heat block 51 made of a metal with good thermal conductivity for heating the column 4; a temperature sensor 511 for detecting the temperature of the heat block 51; and a heater 512 for heating the heat block 51. Also provided are: a door sensor 52 for detecting whether or not outer door 55 of the thermostatic chamber 5 is open; and a lamp 53 or buzzer 54 for warning a user when the heat block 51 is at a high temperature if the outer door 55 is open.

Located within the thermostatic chamber 5 but at its rear portion is a controller unit 7 for controlling various components within the thermostatic chamber 5 of a liquid chromatograph device according to the present invention. The controller unit 7 also performs the control to keep the temperature of the column 4 at a constant temperature. Specifically, the controller unit 7 controls the supply of power from a power source 8 to heater 512 based on the temperature of the heat block 51 detected by a temperature sensor 511.

Figure 2:
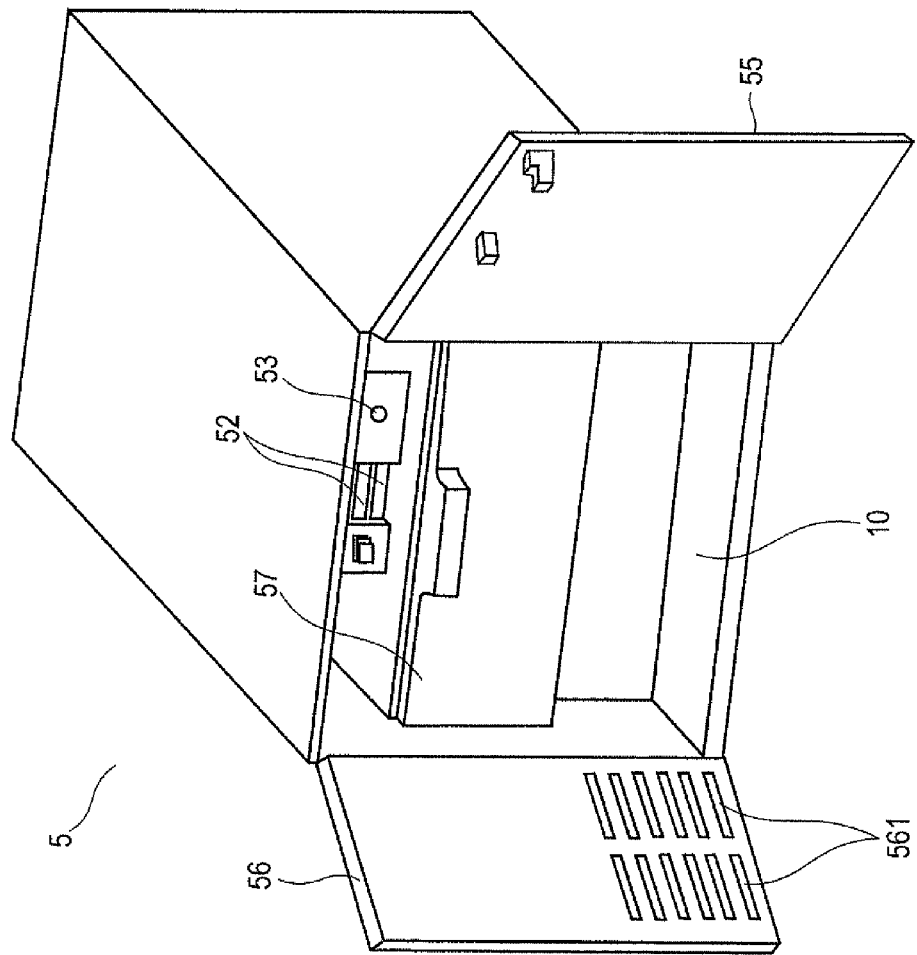
FIG. 2 shows a perspective view of the interior of the thermostatic chamber of a liquid chromatograph device according to the present invention.

FIG. 2 shows a perspective view of a liquid chromatograph device according to the present embodiment with outer doors 55 and 56 of the thermostatic chamber 5 opened. The liquid chromatograph device according to the present embodiment is equipped with two outer doors 55 and 56 at the front face of the thermostatic chamber 5. The construction is such that to open the doors, the door 55 to the right facing the thermostatic chamber 5 is opened first, followed by the opening of the door 56 to the left. To close the outer doors, the door 56 to the left is closed first, followed by the door 55 to the right.

An inner door 57 is provided within the thermostatic chamber 5. The inner door 57 is disposed between the outer doors 55 and 56 and the heat block 51 and prevents user's hands from inadvertently directly touching the heat block 51 when the user opens outer doors 55 and 56 and performs some operation inside the thermostatic chamber 5.

Furthermore, the thermostatic chamber 5 is equipped with two optical door sensors 52 for detecting when the right outer door 55 is open. Two door sensors 52 are provided so that a failure of one is augmented by the sensor function of the other. Disposed at the top of the inner door 57 is an LED lamp 53 which flashes when the heat block 51 is at a high temperature. Furthermore, a buzzer 54 which emits an alarm sound if the inner door 57 is opened when the heat block 51 is at a high temperature is disposed on a circuit board of the controller unit 7 disposed in the thermostatic chamber 5.

Figure 3:
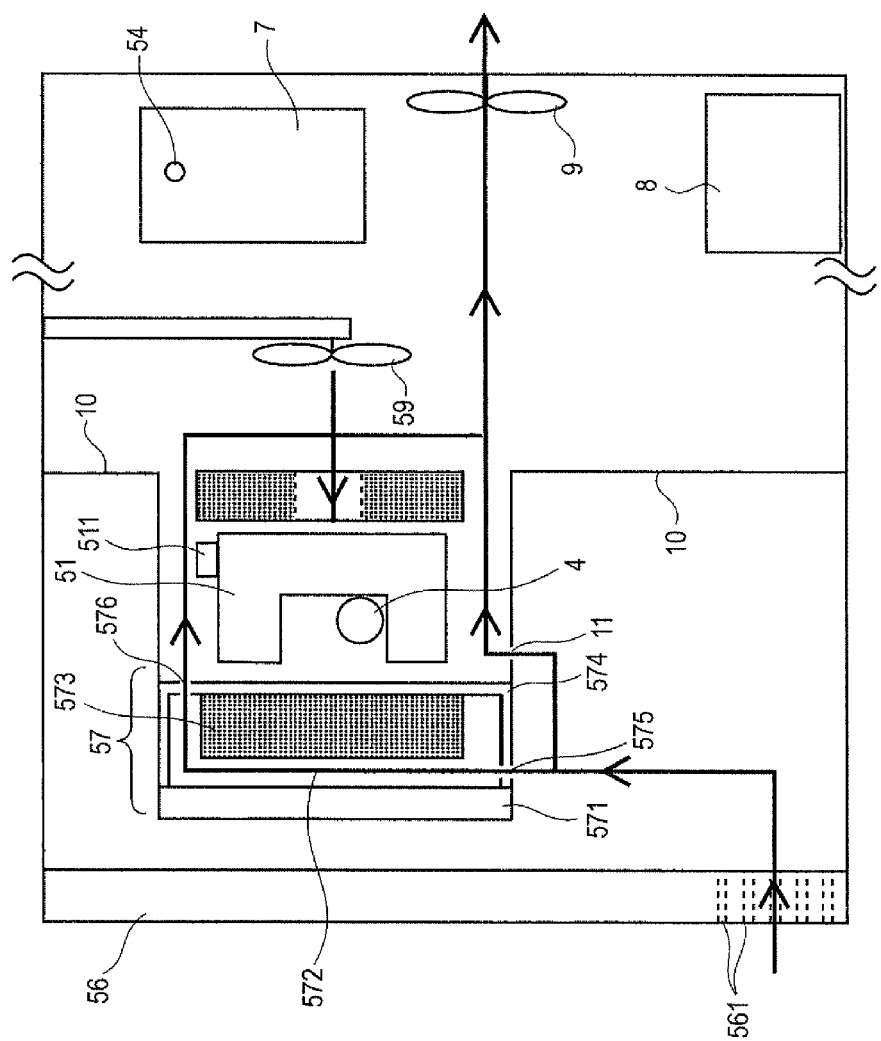
FIG. 3 shows a sectional view of the interior of the thermostatic chamber of a liquid chromatograph device according to the present invention.

FIG. 3 shows a sectional view of the thermostatic chamber 5 of a liquid chromatograph device according to the present embodiment. Heat block 51 and column 4 are disposed in the thermostatic chamber 5 behind inner door 57. The rear area of the heat block 51 is covered by a heat-insulating material 58. A fan 59 is disposed to the rear of the heat-insulating material 58. The central portion of the heat-insulating material 58 is hollowed out, exposing the heat block 51 through the hollowed out section. A fan 9 whose purpose is to cool the entire inner space of the thermostatic chamber 5 is located at the rear of the thermostatic chamber 5. The space within the thermostatic chamber 5 is separated by partition 10 into the front and the rear. The partition 10 extends perpendicularly from the upper and lower inner surfaces of the thermostatic chamber 5 to the general area above and below the heat block heat-insulating material 58 and connects to the top and bottom portions of the inner door 57, following the upper and lower surfaces of the heat block 51. The partition 10 is equipped with a slit 11 at a position directly below the heat block 51.

If a user opens the outer door 55 of the thermostatic chamber 5 while the heat block 51 is being heated, the door sensor 52 detects that the outer door 55 is open and sends a signal to the controller unit 7. When the controller 7 receives the signal indicating that the outer door 55 is open, the controller unit 7 stops the supply of power from the power source 8 to the heater 512 so that the temperature of the heat block 51 does not increase any higher.

The controller unit 7 also uses the temperature of the heat block 51 detected by temperature sensor 511 of the heat block 51 to control the flashing of the lamp 53 and the generation of alarm sound by the buzzer 54. The lamp 53 and the buzzer 54 respectively continue flashing or emitting an alarm sound so long as the temperature sensor 511 (see FIG. 3) is detecting a high temperature while the outer door 55 is open. Specifically, the lamp 53 flashes slowly at a rate of once per second when the detected result by the temperature sensor 511 is between 60° C. and 85° C. and flashes at a faster rate of once per 0.2 seconds when the temperature exceeds 85° C. The buzzer 54 emits an alarm sound when the detected result by the temperature sensor 511 exceeds 60° C. These measures inform the user that the temperature within the thermostatic chamber 5 is high and alerts the user against inadvertently touching the heat block 51 or the inner door 57 with the hands. Since the lamp 53 is disposed more internally in the thermostatic chamber 5 than the outer doors 55 and 56, the flashing of the lamp 53 is visibly apparent to the user even if the user is engaged in some operation with the outer door 55 opened.

When the outer door 55 is opened, the controller unit 7 simultaneously causes the fan 59 located behind the heat block 51 to operate and start cooling the heat block 51. As afore-described, even though the rear portion of the heat block 51 is covered by a heat-insulating material 58, the heat block 51 is partially exposed and allows the airflow from the fan 59 to be directly incident to the exposed portion, thus allowing the heat block 51 to be cooled.

Figure 4:
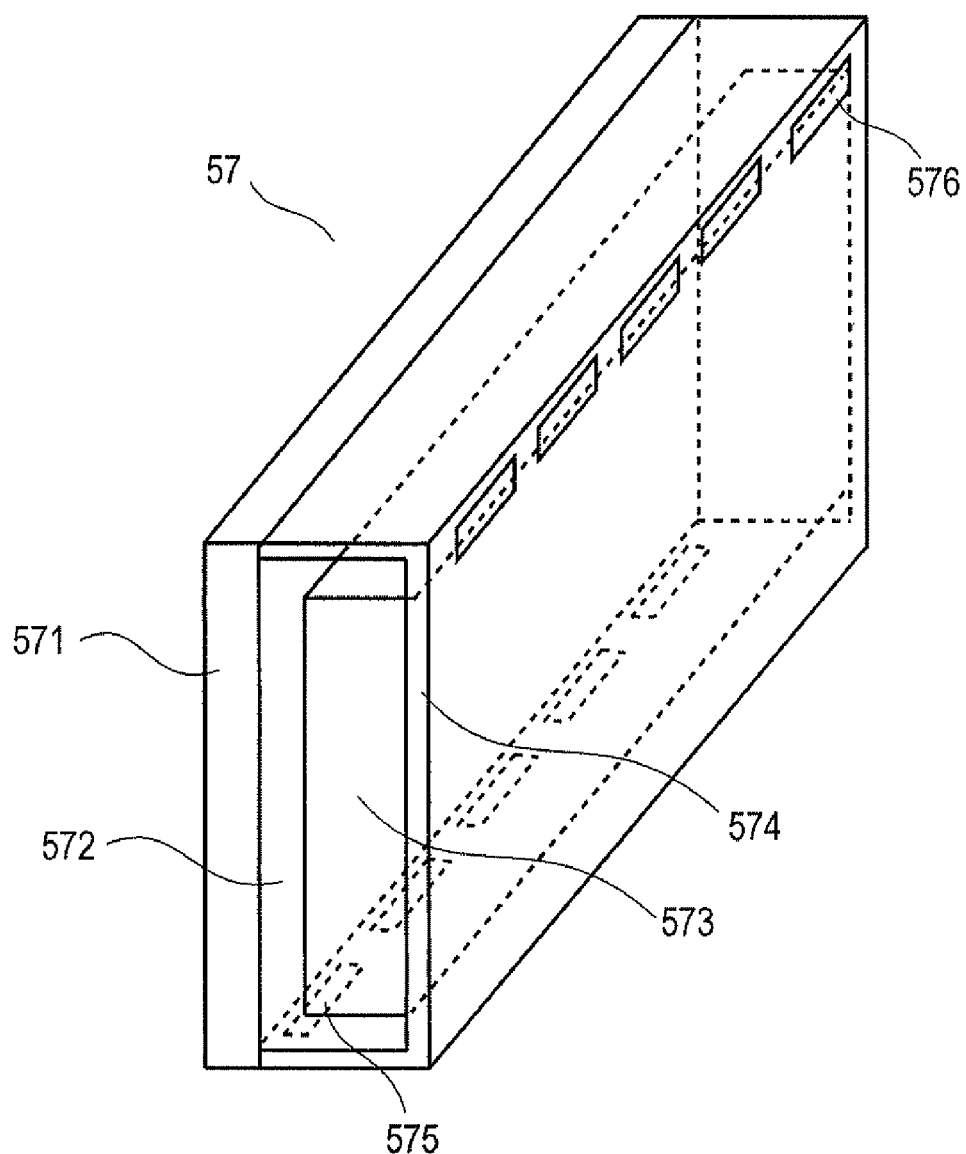
FIG. 4 shows a sectional perspective view of the inner door of the thermostatic chamber according to the present invention.

FIG. 4 shows a sectional perspective view of the inner door 57 of a thermostatic chamber 5 of a liquid chromatograph device according to the present embodiment. The inner door 57 consists of are sin panel 571 and metal panel 574 which form the surfaces of the inner door 57 and a heat-insulating material 573 that is interposed between the resin panel 571 and the metal panel 574. Gaps are provided between the resin panel 571 and the heat-insulating material 573 and at the top and bottom of the heat-insulating material 573, thus forming an air layer 572. A plurality of slits 575 that are provided on the lower surface of the inner door 57 and a plurality of slits 576 that are provided on the upper portion of the rear surface of the inner door 57 respectively connect the air layer 572 to the front portion of the thermostatic chamber 5 and the rear portion of the thermostatic chamber 5.

In FIG. 3, the lines drawn in bold show the airflow within the thermostatic chamber 5. The fan 9 that is disposed in the rear of the thermostatic chamber 5 is always turning while the thermostatic chamber 5 is operating, creating an airflow that moves from the slit 561 that is formed in the outer door 56, through partition slit 11 and to the fan 9, i.e., an airflow that moves from the fore of the partition 10 to its aft. Since the slit 575 formed on the lower surface of the inner door 57 is located to the fore of the partition 10, air from outside the thermostatic chamber 5 that enters through the outer door slit 561 passes through the slit 575 and flows into the space 572 within the inner door and is discharged through upper slit 576 to the space to the rear of the partition 10. Because of the movement of the heated air that is present within the inner door 57, the temperature of the surface resin panel 571 of the inner door 57 is kept below what it is in previous apparatuses. Specifically, when the heat block 51 is heated to 150° C., whereas with the previous device the temperature of the surface resin panel 571 of the inner door 57 was 81° C. and the temperature of the grip portion of the inner door 57 was 63° C., the temperature of the surface resin panel 571 was 42.9° C. and the temperature of the grip portion of the inner door 57 was 38.6° C. with the device according to the present embodiment, showing a large reduction in the surface temperature of the inner door 57. Hence, even if the user were to inadvertently touch the surface resin panel 571 of the inner door 57 with the hand, the risk is greatly reduced.

The afore-described embodiment is just one mode of the present invention, and various modifications and changes are possible without deviating from the scope of the present invention. For example, whereas with the afore-described embodiment the door sensor 52 was an optical sensor, a mechanical or a magnetic sensor may be used. Also, the slit 561 need not necessarily be formed in the outer door 56 and can be formed anywhere in the thermostatic chamber 5 at a place to the fore of the inner door 57. The temperature that is set to cause the operation of the lamp 53 or buzzer 54 can naturally be changed.

DESCRIPTION OF THE NUMERICAL REFERENCES

1. Fluid transport pump
2. Mobile phase vessel
3. Auto-sampler
4. Column
5. Thermostatic chamber
6. Detector
7. Controller unit
8. Power source
9. Fan
10. Partition
11. Partition slit
51. Heat block
52. Door sensor
53. Lamp
54. Buzzer
55, 56. Outer door
57. Inner door
58. Heat-insulating material
59. Fan
511. Temperature sensor
512. Heater
561. Outer door slit
571. Inner door resin panel
572. Inner door air layer
573. Inner door heat-insulating material
574. Inner door metal panel
575, 576. Inner door slit

What is claimed is:

1. A liquid chromatograph device comprising:
a thermostatic chamber;
one or a plurality of outer doors that are disposed at the front surface of said thermostatic chamber;
a heat block that is disposed in said thermostatic chamber for heating a separation column;
a heating means for heating said heat block;
a temperature detection means for detecting the temperature of said heat block;
a flowing means for flowing air between the inside and outside of said thermostatic chamber;
a control means for controlling the supply of power to said heating means based on the detection result of said temperature detection means; and
an inner door between said outer door and said heat block, said inner door comprising a hollow inner door main body, a heat-insulating material that is housed within said inner door main body so as to form an air chamber at least between the heat-insulating material and the surface on the outer door side of said inner door main body, and outlet slits and inlet slits that are formed in said inner door main body;

wherein said flowing means causes air to flow from the outer door side through said inlet slit into said air chamber and air inside said air chamber to flow through said outlet slit to the heat block side.

2. The liquid chromatograph device according to claim 1 further comprising a plurality of outer door open detection means for detecting if, at least, one of said outer doors is open wherein said control means stops the supply of power to said heating means if said outer door open detection means detects that said outer door is open.

3. The liquid chromatograph device according to claim 2 further comprising an alarm sound generation means for generating an alarm sound wherein said control means causes said alarm sound generation means to generate an alarm sound if said outer door open detection means detects that said outer door is open when the temperature detected by said temperature detection means is higher than a predetermined temperature.

4. The liquid chromatograph device according to claim 2 further comprising an alarm display lamp disposed on the front surface of said thermostatic chamber wherein said control means causes said alarm display lamp to flash if said outer door open detection means detects that said outer door is open when the detected result by said temperature detection means is higher than a predetermined temperature.

5. The liquid chromatograph device according to claim 2 further comprising a cooling means for cooling said heat block wherein said control means instructs said cooling means to cool said heat block when said outer door open detection means detects that said outer door is open.

* * * * *